United States Patent [19]

Pons et al.

[11] Patent Number: 4,783,250

[45] Date of Patent: * Nov. 8, 1988

[54] IMMOBILIZED ELECTROCHEMICAL CELL DEVICES AND METHODS OF MANUFACTURE

[76] Inventors: B. Stanley Pons, 2125 South Yuma, Salt Lake City, Utah 84109; Seyed J. Ghoroghchian, 822 Stormy Creek Cir., Sandy, Utah 84070

[21] Appl. No.: 13,691

[22] Filed: Feb. 12, 1987

Related U.S. Application Data

[63] Continuation of Ser. No. 767,919, Aug. 21, 1919, abandoned.

[51] Int. Cl.⁴ .............................................. G01N 27/30
[52] U.S. Cl. .................................... 204/400; 128/635; 204/403; 427/125
[58] Field of Search ............... 204/400, 403, 1 T, 1 K, 204/412; 128/635; 427/125

[56] References Cited

U.S. PATENT DOCUMENTS

| | | | |
|---|---|---|---|
| 3,769,961 | 11/1973 | Fatt et al. | 128/635 |
| 3,824,157 | 7/1974 | Macur | 128/635 X |
| 3,878,830 | 4/1975 | Bicher | 128/635 |
| 3,926,766 | 12/1975 | Niedrach et al. | 204/412 |
| 3,930,493 | 1/1976 | Williamson | 204/400 X |
| 4,225,410 | 9/1980 | Pace | 204/412 |

OTHER PUBLICATIONS

Bas, "1985 Electroanalytical Symposium," pp. 34-36 and 43-47: Abstract Nos. 6-8.
American Chemical Society, *Division of Analytical Chemistry Newsletter* (Jun. 1985).
Marcenac et al., "Fast In Vivo Monitoring of Dopamine Release in the Rat Brain with Differential Pulse Amperometry," *Anal. Chem.*, vol. 57, pp. 1778-1770 (1985).
Joseph, "An Enzyme Microsensor for Urea Based on an Ammonia Gas Electrode," *Analytica Chimica Acta*, vol. 169, pp. 249-256, the Netherlands (1985).
"1985 Abstracts", 1985 *Pittsburgh Conference & Exposition* (Feb. 25 through May 1, 1985), Abstract Nos. 765-768, 773, and 1048-1052.

Curran et al., "Carbon Working Electrode for Liquid Chromatography and Flow Injection Analysis," *Anal. Chem.*, vol. 56, No. 4 (Apr. 1984).
Baranski et al., "Use of Microelectrodes for the Rapid Determination of the Number of Electrons Involved in an Electrode Reaction," *Anal. Chem.*, vol. 57, pp. 166-170 (1985).
Claire, III et al., "Characterization of an On-Column Electrochemical Detector for Open-Tubular Liquid Chromatography,"*Journal of Chromatographic Science*, vol. 23, pp. 186-191 (1985).
Bond et al., "Voltammetric Measurements Using Microelectrodes in Highly Dilute Solutions," *J. Electroanal. Chem.*, vol. 172, pp. 11-25 (1984).
Ewing et al., "Polymer-Coated Microelectrodes and Twin Electrode Thin Layer Cells Applied to Electron Transfer Cross-Reaction and Permeability Rates," *J. Electroanal. Chem.*, vol. 172, pp. 145-153 (1984).

(List continued on next page.)

*Primary Examiner*—G. L. Kaplan
*Attorney, Agent, or Firm*—Shefte, Pinckney & Sawyer

[57] ABSTRACT

Devices and methods for providing electrochemical cells are disclosed which can be used in virtually any gaseous or liquid environment to make electrochemical determinations. The electrochemical cell comprises a microelectrode and a large reference electrode which are positioned a very short distance apart. The space between the microelectrode and the reference electrode is filled with a highly resistant material which has been treated (or otherwise provided) with an ionic substance. In use, the ionic substance associated with the resistive material acts as an immobilized ionic solution in much the same way as an electrolyte in a conventional electrochemical cell. However, the relative size and positioning of the microelectrode and the reference electrode overcame the problems of the prior art so that sensitive, accurate measurements can be obtained in both gas and liquid phase electrochemistry.

4 Claims, 2 Drawing Sheets

OTHER PUBLICATIONS

Howell et al., "Ultrafast Voltammetry and Voltammetry in Highly Resistive Solutions with Microvoltammetric Electrodes," *Anal. Chem.*, vol. 56, pp. 524–529 (1984).

Galus et al., "Electrochemical Behavior of Very Small Electrodes in Solution," *J. Electroanal. Chem.*, vol. 135, pp. 1–11 (1982).

Roullier et al., "Effect of Uncompensated Ohmic Drop in Surface Linear Potential Sweep Voltammetry; Application to the Determination of Surface Rate Constants," *J. Electroanal. Chem.*, vol. 157, pp. 193–203 (1983).

Bond et al., "Electrochemistry in Organic Solvents Without Supporting Electrolyte Using Platinum Microelectrodes," *J. Electroanal. Chem.*, vol. 168, pp. 299–312 (1984).

Scharifker et al., "Electrochemical Kinetics at Microscopically Small Electrodes," *J. Electroanal. Chem.*, vol. 130, pp. 81–97 (1981).

Albery et al., "Transport and Kinetics at Microheterogeneous Electrodes," *J. Electroanal. Chem.*, vol. 131, 137–152 (1982).

Caudill et al., "Flow Rate Independent Amperometric Cell," *Anal. Chem.*, vol. 54, pp. 2532–2535 (1982).

Dayton et al., "Faradaic Electrochemistry at Microvoltammetric Electrodes," *Anal. Chem.*, vol. 52, pp. 946–950 (1980).

Wightman, "Microvoltammetric Electrodes," *Anal. Chem.*, vol. 53, No. 9, pp. 1125A–1133A (1981).

Aoki et al., "Diffusion Controlled Current at a Stationary Finite Disk Electrode," *J. Electroanal. Chem.*, vol. 125, pp. 315–320 (1981).

Kissinger, "Amperometric and Coulometric Detectors for High-Performance Liquid Chromatography," *Anal. Chem.*, vol. 49, No. 4, pp. 446A–456A (1977).

Lines et al., "Voltammetry in Benzene and Chlorobenzene. The Behaviour of Ions of Aromatic Compounds in Nonpolar Media," *Acta Chem. Scand.*, B 31, No. 5, pp. 369–374 (1977).

Gueshi et al., "Voltammetry at Partially Covered Electrodes Part II. Linear Potential Sweep and Cyclic Voltammetry," *J. Electroanal. Chem.*, vol. 101, pp. 29–38 (1979).

IMMOBILIZED ELECTROCHEMICAL CELL DEVICES AND METHODS OF MANUFACTURE

This is a continuation of application Ser. No. 767,919, filed Aug. 21, 1985 and now abandoned.

BACKGROUND

1. The Field of the Invention

This invention relates to devices and methods for use in connection with electrochemical analyses and determinations and, more particularly, to novel devices and methods which are capable of being used in liquid or gaseous environments to induce, detect, and monitor electrochemical oxidation/reduction reactions.

2. The Prior Art

It is a well-known principle of science that the atoms and molecules of most substances, except air and a number of pure solvents, will undergo an electrochemical reaction in the presence of a strong electric field. This electrochemical reaction is characterized by the atom or molecule either losing or gaining one or more electrons in a process known as ionization. If the atom or molecule loses one or more electrons in the electrochemical reaction, it is said to have been "oxidized." If, on the other hand, the atom or molecule gains one or more electrons during the electrochemical reaction, it is said to have been "reduced."

For example, a chlorine molecule is composed of two chlorine atoms and is electrically neutral. In other words, the chlorine molecule does not naturally have an associated electrical charge. In the presence of a strong electric field, however, the chlorine molecule will be reduced by gaining two electrons. The chlorine molecule is thereby transformed into two chloride ions, each of which is negatively charged.

The analysis and detection of electrochemical oxidation or reduction reactions has many important uses. Many forms of chemical analysis are, for example, dependent upon the accurate detection and quantitative measurement of electrochemical reactions. In addition, the study of electrochemical reactions has several important uses in research and development activities.

For example, the magnitude of the electric field which is required in order to cause a particular atom or molecule to undergo oxidation or reduction varies with each chemical compound. Thus, if one can measure the magnitude of the electric field at which a compound is oxidized or reduced, it is often possible to identify the particular compound.

In addition to determining the identity of a substance which is being oxidized or reduced, the electrochemical reaction can be monitored over time so as to determine the concentration of the material which is undergoing the reaction. This follows from the fact that the rate at which atoms or molecules of a material are oxidized or reduced is proportional to the concentration of the material in the environment.

To determine the identity and concentration of a particular material may, of course, be important in several contexts. For example, it may be desirable to identify impurities in a mixture, such as, for example, in a public water supply. It may also be important to detect the presence of certain harmful substances and determine the concentration of such substances. The monitoring and analysis of electrochemical reactions is, thus, often used for many of these purposes.

In the course of research and development, it is often useful to study the oxidation and reduction of various substances. For example, electric batteries use oxidation and reduction reactions to supply an electric current. The amount of current which can be delivered by the battery is limited by the speed at which the materials within the battery can be oxidized and reduced. Thus, in an effort to develop better, higher current density batteries, it would be important to identify those materials which are oxidized and reduced most rapidly.

The magnitude of the electric field which is required to cause an atom or molecule to undergo either oxidation or reduction is very substantial. Typically, the magnitude of this electric field must be in the order of between 100 million ($10^8$) volts per centimeter to one billion ($10^9$) volts per centimeter. In other words, if two electrodes are placed one centimeter apart in a vacuum, the electric potential difference between the two electrodes would need to be between 100 million volts and one billion volts in order to create an electric field of sufficient strength to cause an atom or molecule to undergo oxidation or reduction.

Obviously, it is both unsafe and uneconomical in most cases to provide the magnitude of electric field required for oxidation or reduction by simply providing two electrodes with a large difference in electric potential. Accordingly, those skilled in the art have conventionally used a device called an electrochemical cell.

A typical electrochemical cell comprises two electrodes which are immersed in a solvent, such as, for example, water. An ionic substance (commonly called the "electrolyte") is then dissolved in the solvent. The ionic substance is one which dissociates upon being dissolved in a solvent into charged atoms or molecules which are called "ions." This is, for example, a characteristic of virtually all salts. Thus, if water is used as a solvent in an electrochemical cell, a suitable salt, such as, for example, sodium chloride ("NaCl"), may be dissolved in the water to serve as the electrolyte.

In operation, an electric potential is imposed between the two electrodes in the cell solution. One of the electrodes will, of course, have a relative positive charge, and the other electrode will have a negative charge. These charged electrodes in turn attract the ions in the solution which have the opposite charge. Thus, the positively charged electrode will attract negatively charged ions and vice versa.

After a brief time period, a sufficient number of ions will have collected adjacent each electrode so as to form a compact and diffuse charged layer of ions. Provided there is a sufficient amount of electrolyte in the solution, the layer of ions will have a total charge which is equal in magnitude, but opposite in polarization, to the charge of the electrode. The ion layer thus balances the charge of the electrode so that the electrode does not have any significant effect on particles within the electrochemical cells which are located a great distance from the electrode. In other words, the electrode becomes electrically isolated from the solution by means of the charged ion layer.

The charged ion layer is typically located approximately one to three angstroms (100 millionths of a centimeter) away from the electrode. The charged ion layer thus simulates a second oppositely charged electrode positioned parallel to the electrode with a very small distance therebetween. The region between the real electrode and the imaginary, parallel electrode is often referred to as the electrical "double layer."

As previously indicated, the magnitude of an electric field may be expressed as the difference in electric potential per unit distance. Using this definition, it can be readily appreciated that a small difference in potential between the electrode and the solution in the electrochemical cell will create a very high magnitude electric field in the region of the double layer described above.

For example, there may be a one volt electric potential difference between the electrode and the solution in the electrochemical cell. From the foregoing discussion, it will be appreciated that this entire change in potential takes place over the distance of the double layer surrounding the electrode.

Further, as previously indicated, the double layer is typically on the order of from one to three angstroms thick. Thus, even a potential difference of one volt between the electrode and the solution in the cell will create an electric field having a magnitude on the order of 100 million volts per centimeter in the region of the double layer. A potential difference of one volt is, of course, easy to obtain. Accordingly, it is quite feasible to create in the double layer region of an electrochemical cell an electric field having a sufficient magnitude to cause a reduction/oxidation ("redox") reaction.

To illustrate this, suppose an electrochemical cell contained a number of benzene molecules. As benzene molecules enter a "positive" double layer region adjacent the electrodes, the molecules would be in an electric field of sufficient magnitude to cause the benzene molecules to lose an electron and undergo an oxidation reaction.

Importantly, the configuration of the electrochemical cell is readily adapted to monitor redox reactions and detect that they are occurring. In the foregoing example, the benzene molecules would lose an electron, as already noted. At the same time, an atom or molecule adjacent the other electrode in the electrochemical cell would gain an electron, and a current would, therefore, flow through the circuit connecting the two electrodes. Accordingly, by monitoring the current in the circuit between the two electrodes, one can easily detect and monitor the redox reaction.

In using an electrochemical cell of the type described above for purposes of analysis, one might gradually increase the potential difference between the electrode and the solution until a current is detected in the external circuit, thereby indicating that a redox reaction is taking place. This potential difference is referred to as the "redox potential" of the substance which is undergoing the redox reaction. Fortunately, redox potentials are well documented. Therefore, after determining the redox potential of the substance, one may be able to identify the substance which is in the electrochemical cell.

In addition, the magnitude of the current in the external circuit between the two electrodes is an indication of the frequency at which redox reactions are taking place. The number of redox reactions which take place during a given period of time is an indication of the concentration of the substance undergoing the redox reaction. Accordingly, by monitoring the current in the external circuit, one may also determine the concentration of the substance within the electrochemical cell.

The typical, elementary electrochemical cell described above is easy to construct and use. Nevertheless, there are a number of obstacles to overcome in using such an electrochemical cell to obtain accurate results.

The first significant obstacle arises from the fact that it is theoretically impossible to measure the potential of a single electrode; only differences in potential can be measured. The potential is then usually measured against a standard reference electrode. If the reference electrode is subjected to large currents, however, such as those found in the elementary two-electrode electrochemical cells described above, the standard potential of the reference electrode will change.

In order to correct this situation, those skilled in the art typically make one of the electrodes (the "working electrode") very small, while making the other electrode (the "reference electrode") massive in comparison. In this way, the current per unit area is kept quite small, and the reference electrode potential does not significantly change.

Often, however, even small changes in the reference electrode potential are unacceptable. In these cases, it then becomes necessary to use a third electrode which is not a part of the electrochemical circuit as a reference electrode. The use of such a third electrode, however, complicates the electrical circuitry and makes the system somewhat more difficult to calibrate and use.

Additionally, since the error in making the potential measurements is directly proportional to the current through the system, high currents in the system also lead to a high degree of error in measuring the potential. Moreover, the error in potential measurement is also directly proportional to the resistance of the system, and the resistance of the system is typically quite high. This situation compounds thus the problem and makes the error in measuring potential still higher.

In an effort to reduce the error in potential measurement caused by the high current, those skilled in the art typically try to reduce the resistance of the system. This is done by adding a large amount of the electrolyte which makes the solution of the electrochemical cell more electrically conductive. By increasing the conductivity of the solution, and thereby reducing its resistance, it is hoped that the potential error can be brought down to acceptable limits even in the presence of relatively large currents.

In addition to the relatively large currents in the system which have already been mentioned, there is a large capacitive current associated with the movement of ions in the solution toward the two electrodes to develop the double layer. This current is typically very large and, in some cases, can totally drown out the current caused by the redox reaction which one is attempting to measure.

To reduce the difficulties caused by the large capacitive current, those skilled in the art again relay upon the use of large amounts of electrolyte. By introducing a large number of charged ions into the electrochemical cell, the ions do not have to move far in the solution before the working electrode is properly balanced by an ionic layer. Accordingly, the working electrode can be electrically isolated quickly, thereby reducing the interference of the capacitive current on the measurement being made.

An additional difficulty with conventional electrochemical cells arises from the mechanism by which the redox reaction proceeds over time. As the electrochemical cell is first energized at the appropriate potential, atoms and molecules which are immediately adjacent the working electrode are quickly depleted from the double layer region as they undergo a redox reaction. After this initial surge of activity, one must wait until additional atoms and molecules can diffuse through the electrochemical cell toward the working electrode. As a typical result, the reading from an electrochemical cell stepped between two potentials shows an initial surge of high current which thereafter drops down to a lower current reading.

In many cases, the initial transient high current reading may interfere with the analysis being done, and it may be desirable to maintain a steady state throughout the reaction. Accordingly, since the rate of the redox reaction depends somewhat on the voltage drop across the double layer, it is typical to approach a steady state situation by decreasing the speed at which the voltage across the double layer is changed over the course of a given analysis. In this way, it is hoped that the readings can approach a steady state condition at virtually all voltage levels.

A somewhat more troublesome consequence of the rapid depletion of atoms and molecules from the double layer is that it becomes difficult to study the kinetic limit of the reaction. The kinetic limit of the redox reaction is the maximum speed at which the redox reaction can occur if there is an unlimited supply of the substance being reduced or oxidized. As mentioned previously, studying the kinetic limits of particular reactions is important in many research and development applications, such as, in the development of high current density power supplies.

Unfortunately, in conventional electrochemical cells, the rate at which the redox reaction takes place is not limited by the actual speed of the reduction but is, rather, limited by the speed at which atoms and molecules can diffuse through the electrochemical cell solution. This situation is worsened by the fact that most electrodes are essentially planar and atoms and molecules can, therefore, only approach the electrode from one direction. This further retards the diffusion rate and limits the speed of the redox reaction.

Some attempts to approach the kinetic limits of a reaction have been made by changing the geometry of the electrode. For example, if the electrode is shaped spherically, atoms and molecules can approach the electrode from virtually any direction. This results in the atoms and molecules diffusing toward the electrode at a much higher rate.

In addition, when attempting to study the kinetics of the reaction, it has become quite common to use rotating or otherwise agitated electrodes. By rotating the electrode through the electrochemical cell, one is not limited solely by diffusion, since the movement of the electrode itself serves to bring atoms and molecules into contact with the working electrode.

In summary, while conventional electrochemical cells are adequate for many applications, there use in some situations of prime interest is very complex. Not only can it be difficult to set up the electrochemical cell with all of the required compensations for error, but the complexity of the system also increases the probability of some human errors. Accordingly, those skilled in the art have attempted to build electrochemical cells which are simpler in construction and which avoid the disadvantages set forth above.

One promising developing in recent years has been the use of a very small electrode as the working electrode in an electrochemical cell. These very tiny electrodes have come to be known as "microelectrodes."

Microelectrodes draw a very small current. As a result, the error in measuring the potential in the system is reduced. Consequently, it may often not be necessary to use a third reference electrode when making electrochemical measurements.

Also, since the size of the working microelectrode is extremely small, only a very few ions are needed to electrically isolate the electrode in the electrochemical call. Accordingly, there is a much smaller capacitive current in the electrochemical call to interfere with accurate readings.

Further, as the microelectrode approaches atomic proportions, the electrode begins to act much more like a hemisphere-shaped electrode. Accordingly, atoms and molecules are able to diffuse toward the electrode from several different directions, thereby decreasing the limitation caused by the rate of diffusion.

In spite of these advantages, however, electrochemical cells which are currently being used suffer from a number of significant drawbacks. First, all of the electrochemical cells which are currently in use require some type of liquid solvent in which an electrolyte is dissolved. This, of course, limits the application of the electrochemical cell to the liquid phase.

Similarly, the structure and configuration of prior art electrochemical cells with their liquid solvents and electrolytes virtually eliminates many potential uses of electrochemical cells. For example, electrochemical cells cannot presently be used to test a substance in a gaseous environment. Rather, the substance to be tested must typically be sampled and then returned to the laboratory for analysis.

BRIEF SUMMARY AND OBJECTS OF THE INVENTION

In view of the foregoing, it is a primary object of the present invention to provide electrochemical cell devices and methods which do not require the purposeful addition of electrolyte in order to make electrochemical measurements.

It is also an object of the present invention to provide electrochemical cell devices and methods which may be used in gaseous, as well as liquid, environments.

Additionally, it is another object of the present invention to provide devices and methods for electrochemical cells which are sensitive, accurate, and simple and economical to manufacture and operate.

It is a further object of the present invention to provide electrochemical cell devices and methods which give only a small error in the potential reading even in a high resistive environment.

Further, it is an important object of the present invention to provide electrochemical cell devices and methods wherein the capacitive current is small and does not interfere with the measurements being made.

Also, it is an object of the present invention to provide electrochemical cell devices and methods which are capable of giving steady state readings even with rapid variations in potential.

It is an additional object of the present invention to provide dependable electrochemical cell devices and methods which can be used to study the kinetic limits of redox reactions but which do not require complex machinery or rotating parts.

It is a still further object of the present invention to provide electrochemical cell devices and methods which achieve near perfect spherical diffusion.

Also, it is an object of the present invention to provide electrochemical cell devices and methods which may be easily used to distinguish between substances based upon their redox potentials.

Consistent with the foregoing objects, the present invention is directed to devices and methods for providing electrochemical cells which can be used in virtually any gaseous or liquid environment to make electrochemical determinations. The electrochemical cell comprises a microelectrode and a large reference electrode which are positioned a very short distance apart. The space between the microelectrode and the reference electrode is filled with a highly resistive insulating material, which has been treated (or otherwise provided) with an ionic substance.

In use, the ionic substance associated with the resistive material acts as an immobilized ionic solution in much the same way as an electrolyte in a conventional electrochemical cell. However, the relative size and positioning of the microelectrode and the reference electrode overcome the problems of the prior art so that sensitive, accurate measurements can be obtained in both gas phase and liquid phase electrochemistry.

These and other objects and features of the present invention will become more fully apparent from the following description and appended claims, taken in conjunction with the accompanying drawings.

DETAILED DESCRIPTION OF THE PREFERRED EMBODIMENTS

It will be readily appreciated that the components of the present invention, as generally described and illustrated in the figures herein, could be arranged and designed in a wide variety of different configurations. Thus, the following more detailed description of the embodiment of the apparatus and methods of the present invention, as represented in FIGS. 1 through 4, is not intended to limit the scope of the invention, as claimed, but it is merely representative of one presently preferred embodiment of the invention.

The presently preferred embodiments of the invention will be best understood by reference to the drawings, wherein like parts are designated with like numerals throughout.

1. General Discussion

Figure 1:
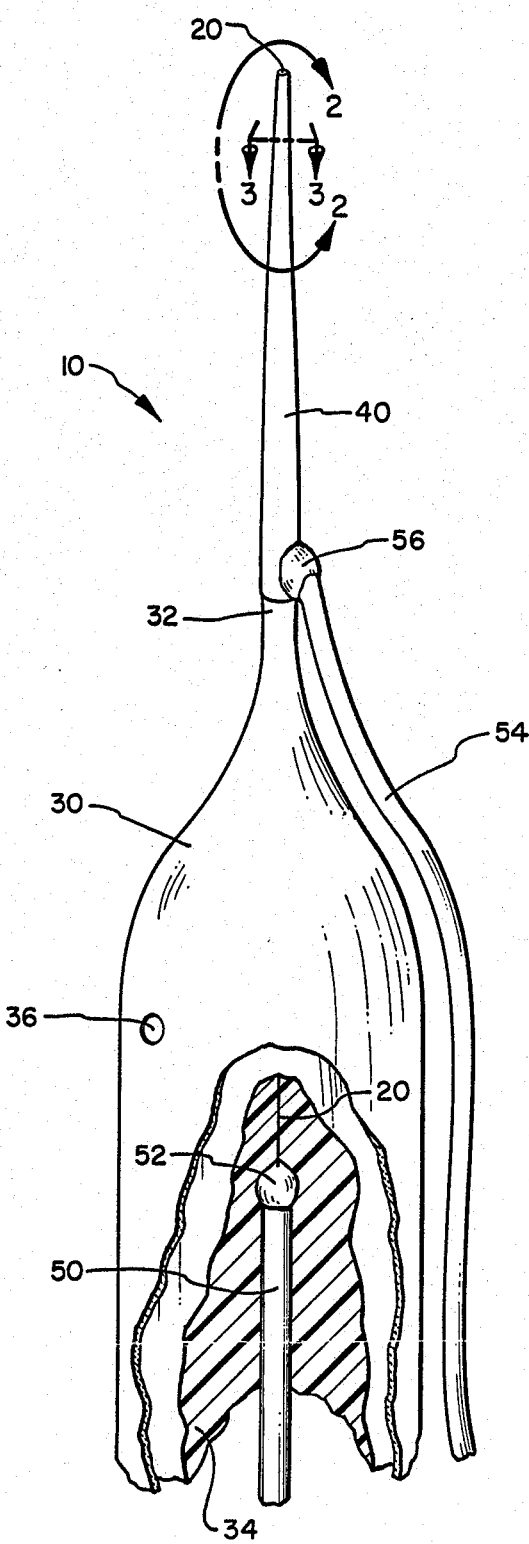
FIG. 1 is a perspective view of one presently preferred embodiment of the immobilized electrochemical cell of the present invention, with parts of the device being broken away to reveal its interior construction.
Figure 2:
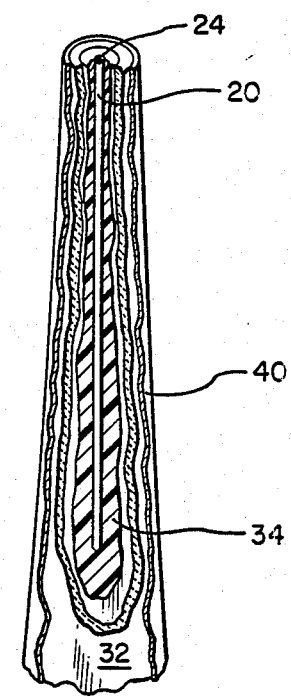
FIG. 2 is a partial perspective view taken along lines 2—2 of FIG. 1, with parts being broken away to reveal the internal construction.
Figure 3:
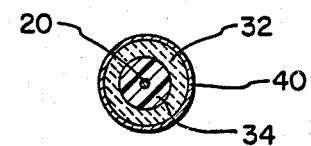
FIG. 3 is a vertical cross-sectional view taken along lines 3—3 of FIG. 1.

One presently preferred embodiment of the immobilized electrochemical cell of the present invention, designated generally at 10, is depicted in FIGS. 1-3. As shown, electrochemical cell 10 comprises a working microelectrode 20 and a large reference electrode 40. The space between microelectrode 20 and reference electrode 40 is filled with one or more layers 32 and 34 of insulator material which is sufficiently conductive so as to function as an electrolyte.

Significantly, the electrolyte portion of electrochemical cell 10 of the present invention is immobilized between microelectrode 20 and reference electrode 40. As a result, electrochemical cell 10 may be placed in any gaseous or liquid environment to make electrochemical measurements and determinations. Moreover, because the insulator material between microelectrode 20 and reference electrode 40 acts as an electrolyte, the environment into which electrochemical cell 10 is placed need not have any added electrolyte of its own.

A brief review of the performance characteristics of electrochemical cell 10 is set forth below. This discussion illustrates that the electrochemical cell functions quite accurately without the complex compensation mechanisms and adjustments which are required in electrochemical cells of the prior art.

The limiting current to a spherical electrode is given by the equation:

$$I_{limit} = nFCDA \left| \frac{1}{\sqrt{\pi Dt}} + \frac{1}{r} \right|; \qquad (1)$$

where
$I_{limit}$ is the limiting current;
n is the number of electrons;
F is the Faraday constant;
C is the concentration;
D is the diffusion coefficient;
A is the surface area of the electrode;
r is the radius of the sphere; and
t is the elapsed time.
If diffusion is the only mode of mass transport to the electrode, the time-dependent term in the above equation approaches zero over time. Thus, if the radius of the electrode is very small, the time dependent term will quickly become negligible, and the current will be governed by the radius of the microelectrode. Therefore, equation (1) reduces to:

$$I_{limit} = \frac{nFCDA}{r}. \qquad (2)$$

Further, in such a case, the limiting current for a disc microelectrode is approximately:

$$I_{limit} = 4nFDCr_d \qquad (3);$$

where $r_d$ is the radius of the disc.

From equation (3), it can be seen that the limiting current will be extremely small for small sizes of the electrode. This does not pose a significant problem, however, since present instrumentation makes it possible to measure currents down to $10^{-18}$ amps, which is approximately 1 electron transfer per second. Moreover, the small current helps the reference electrode maintain a potential which is extremely close to the potential of the surrounding environment, thereby eliminating the need for a separate reference electrode.

Additionally, the small magnitude of the current reduces the error in measuring the potential difference between the microelectrode and reference electrode, since the error in potential is proportional to the current.

The error in potential is further reduced by the fact that microelectrode 20 and reference electrode 40 are spaced only a very short distance apart, and the resistance between them is, therefore, relatively small. This is due to the fact that the resistance of the system is increased as the distance between microelectrode 20 and reference electrode 40 is increased. Thus, the small distance between the two electrodes, coupled with the small current in the system, gives rise to a very small potential error.

It is most desirable to have a potential error of less than approximately 1 millivolt (mV). Because of the foregoing considerations, this is easily accomplished with the present system. Moreover, because of the simplicity of the present system, it is now possible to calculate the potential error, something which could not be done with the prior art systems.

With a spherical electrode, the ohmic potential error is:

$$\Delta y_{ohmic} = \frac{RT}{F} \frac{D_R}{(D_+ + D_-)D^*} \operatorname{Ln}\left\{\frac{\left(1 - \frac{r_s}{b}\right)C_o^b\, b \exp\left(\frac{y^\theta F}{RT}\right) + D^* C_R^b \left[b \exp\left(\frac{y^\theta F}{RT}\right) - r_s\right]}{\left(1 - \frac{r_s}{b}\right)C_o^b\, b \exp\left(\frac{y^\theta F}{RT}\right) + D^* C_o^b\, b \left(1 - \frac{r_s}{b}\right) + D^* C_R^b\, r_s \left[\exp\left(\frac{y^\theta F}{RT}\right) - 1\right]}\right\} \quad (4)$$

where
- $\Delta y_{ohmic}$ = ohmic potential drop (V),
- R = the gas constant (J °K$^{-1}$ mole$^{-1}$),
- T = temperature (°K),
- t+ = cationic transport number,
- F = the Faraday constant (C mole$^{-1}$)
- D* = parameter related to diffusion coefficient (dimensionless),
- $C_R^b$ = bulk concentration of species R at r = b (mole m$^{-3}$),
- b = distance from the working electrode to the counter electrode (m),
- r = radial distance from the center of the electrode (m),
- $C_o^b$ = bulk concentration of species O (mole m$^{-3}$),
- $\gamma^\theta$ = standard concentration overpotential (V),
- $r_s$ = radius of spherical electrode (m),
- $D_+$ = diffusion coefficient of cations (m$^2$ sec$^{-1}$),
- $D_-$ = diffusion coefficient of anions (m$^2$ sec$^{-1}$), and
- $D_R$ = diffusion coefficient of species R (m$^2$ sec$^{-1}$).

If $r_s$ (radius of the sphere) is much less than the distance between the electrodes, equation (4) reduces to:

$$\Delta y_{ohmic} = \frac{2RTt+}{F} \operatorname{Ln}\left\{\frac{[D^* C_R^b + C_o^b]\exp\left(\frac{y^\theta F}{RT}\right)}{\left[D^* + \exp\left(\frac{y^\theta F}{RT}\right)\right]C_o^b}\right\} \quad (5)$$

A similar equation can be written for the microdisc electrode using the following relationship:

$$r_s = \frac{\pi}{4} r_d;$$

where
- $r_s$ equals the radius of the sphere; and
- $r_d$ equals the radius of the disc.

It will also be appreciated that the capacitive current associated with the migration of ions toward microelectrode 20 is quite small. This follows from the fact that the capacitive current is directly proportional to the surface area of the electrode. Accordingly, since microelectrode 20 has a very small exposed surface area (as shown at 24 in FIG. 2), the capacitive current will be small and will not interfere with the measurements being made.

Mass transport is so fast per unit area that the electrochemical reaction is not dependent on the rate of mass transport. Thus, the microelectrode of the present invention is kinetically limited and always at a steady state.

As a further result of the small size of the microelectrode, atoms and molecules can approach the microelectrode from a variety of directions. As a result, diffusion is not always the limiting factor in the electrochemical reaction, except for very fast reactions.

The ease with which an atom or molecule may approach an electrode is often quantified in the form of a "mass transfer coefficient." The greater the mass transfer coefficient, the easier it is for an atom or molecule to approach the electrode. The mass transfer coefficient for a microsphere is given by:

$$K_m = \frac{D}{r_s}; \quad (6)$$

where:
- $K_m$ is the mass transfer coefficient;
- D is the diffusion coefficient; and
- $r_s$ is the radius of the sphere.

For a microdisc this becomes:

$$K_m = \frac{4D}{\pi r_d}; \quad (7)$$

where: $r_d$ is the radius of the disc.

From equation (7), it will be appreciated that the mass transfer coefficient is quite large as the radius of the disc microelectrode becomes smaller. As the radius of the disc microelectrode becomes very small, therefore, the system approaches near perfect spherical diffusion.

In fact, in the case of electrochemical cell 10 of the present invention, the system approaches the point where diffusion is very often not the limiting factor at all. Rather, the atoms and molecules to be oxidized or reduced are effectively surrounding the electrode waiting to come to double layer region surrounding microelectrode 20. In this situation, it is very easy to study the kinetics of the redox reaction in an effort to determine the speed at which an electron may jump from the reactant atom or molecule to microelectrode 20 or vice versa.

2. Electrochemical Cell Configuration

Referring now to FIGS. 1–3, electrochemical cell 10 comprises a microelectrode 20 which is surrounded by one or more layers 32 and 34 of highly resistive insulating material, and a reference secondary electrode 40. Each of these components is discussed separately below.

Microelectrode 20 is formed so as to have a very small cross-sectional diameter. In order to avoid the problems of large currents, diffusion limitations, and large potential errors discussed above, the microelectrode preferably has a cross-sectional diameter of no more than approximately 25 microns. It is presently preferred that the microelectrode have a cross-sectional diameter within the range of from about 100 angstroms to about 10 microns.

Within the foregoing size limitations, microelectrode 20 may have a number of different configurations. For example, microelectrode 20 may comprise a fine wire or fiber. In this case, microelectrode 20 forms a working electrode disc 24 (see FIG. 2).

Alternatively, the microelectrode may be formed by coating a conductive material on a holder. For example, a conductive material has been deposited on a thin glass fiber. This could be accomplished by a number of means which are presently known in the art, such as, for example, by vapor deposition or screen printing techniques.

Figure 3A:
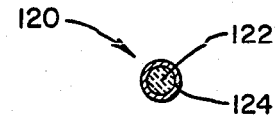
FIG. 3A is a cross-sectional view of an alternate embodiment of the microelectrode of the electrochemical cell of the present invention.

A microelectrode 120 which is formed on a holder in the manner described above is illustrated in FIG. 3A. As shown, the inside of microelectrode 120 comprises a glass material 122 which is surrounded by a conductive layer 124. As depicted in FIG. 3A, microelectrode 120 thus forms a ring-shaped working electrode when exposed at the end of electrochemical cell 10.

There are, of course, countless other ways in which a very small size electrode could be provided. For example, conventional photolithographic processes could be employed so as to provide a microelectrode on a substrate chip.

The material which is used to form microelectrode 20 may be made of any suitable conductive material. For broad applications, it is presently preferred that platinum, palladium, and gold be employed. However, carbon fibers, silver, nickel, zinc, iron, copper, cobalt, and magnesium will also give satisfactory results under specific conditions.

As shown in FIGS. 2 and 3, one or more layers 32 and 34 of an insulating material surround microelectrode 20. This insulating material should preferably by made as thin as possible so as to minimize the resistance in the system between microelectrode 20 and reference secondary electrode 40. Thus, depending on the conductivity of the insulating material, layers 32 and 34 are preferably less than a total of approximately 2-3 millimeters thick. It is presently preferred that layers 32 and 34 have a thickness totaling no more than approximately 0.5 millimeters thick.

The required insulating layer may be formed of any suitable high resistance material. For example, the insulating layer may comprise a glass tube 30 have a capillary end portion 32 which is sealed around microelectrode 20.

Glass material 32 may be sealed around microelectrode 20 in any of a number of ways. For example, glass material 32 could be melted so as to be sealed directly around microelectrode 20. An easier approach, however, is to use some type of separate sealing material.

As depicted in FIGS. 2 and 3, sealing material 34 may be forced between glass material 32 and microelectrode 20 so as to completely enclose microelectrode 20 in an insulative material. Sealing material 34 may comprise any suitable high resistance substance. For example, sealing material 34 may comprise epoxy, plastic, glass cement, jewelers wax, or any of a number of commercially available ceramic adhesives.

Importantly, layers 32 and 34 must have a high enough conductivity to allow them to function as an electrolyte. Typically, if microelectrode 20 is less than approximately 2500 angstroms in diameter, there is usually enough ionic material in the insulator material itself and/or in the surrounding environment to achieve the necessary conductivity. However, microelectrodes of less than 2500 angstroms in diameter are quite difficult to make.

In the case of larger microelectrodes, it is necessary to add an ionic substance to glass layer 32 and sealant layer 34 to increase their conductivity. This may, for example, by done by incorporating some type of an ionic substance into the materials during their manufacture. Alternatively, the conductivity of layers 32 and 34 may be increased by using an ionic coating.

An ionic coating is preferably applied to the exposed portions of layers 32 and 34 which surround disc 24 of microelectrode 20 (see FIG. 2). This coating is, for example, preferably in the form of a solution comprising, e.g., sodium hydroxide, potassium hydroxide, lithium hydroxide, guanadine, pyridine, quinoline, hydrofluoric acid, hydrochloric acid, hydroiodic acid, sulphuric acid, iodine, bromine, chlorine, hydrocyanic acid, or salts of any of the foregoing acids and bases.

While it is presently not known exactly how these coatings function, it is believed that they break up the exposed surface of layers 32 and 34 such that organic salts are chemically attached thereto. This is confirmed by the fact that it has been found that electrochemical cell 10 may be washed and reused numerous times without losing its effectiveness. Regardless of the specific functional mechanism, however, any ionic coating or layer which allows layers 32 and 34 to function as an electrolyte is intended to be within the scope of the present invention by the doctrine of equivalents.

Reference secondary electrode 40 is coated around layers 32 and 34. The specific size of reference secondary electrode 40 is not critical, and it should preferably be made as large as practicable. For example, reference secondary electrode 40 may have a surface area of as large as 1 square centimeter or more.

The material which is used to form reference electrode 40 may be any suitable conductive material. It is presently preferred, however, that reference electrode 40 be formed of a noble metal so as to prevent corrosion. For broad applications, as with microelectrode 20, it is preferred that reference electrode 40 be comprised of platinum, palladium, or gold. However, other suitable materials include nickel, copper, carbon, silver, and iron.

Reference secondary electrode 40 may be placed around insulative layers 32 and 34 in any of a number of ways. For example, reference secondary electrode 40 may be vapor deposited or screen printed on glass layer 32.

Prior to use, it is, of course, necessary to electrically connect electrochemical cell 10 to the external circuit. This may be accomplished by means of wires which are connected to microelectrode 20 and reference electrode 40.

For example, as shown in FIG. 1, a wire 50 may be soldered or connected by means of silver epoxy at 52 to microelectrode 20. Similarly, a wire 54 may be soldered or connected by means of silver epoxy at 56 to reference electrode 40. Wires 50 and 54 can then be readily connected to the external circuitry.

Alternatively, an electrical connection with microelectrode 20 may be made by means of a conductive material which fills glass tube 30. For example, if microelectrode 20 is formed of carbon or platinum, mercury may be placed inside of glass tube 30 so as to make electrical contact with microelectrode 20.

As previously noted, the currents which have been detected by electrochemical cell 10 are very small. As a result, interference may arise due to the presence of radio frequency signals and other electrical signals in the surrounding environment. Accordingly, it may be desirable to place electrochemical cell 10 within a shielding box or cage, often referred to as a Faraday cage, such that it is effectively shielded from such interference.

In many instances, it may also be desirable to coat electrochemical cell 10 with some type of screening polymer. Screening polymers are well known in the art and may be used to prevent one or more substances from coming into contact with microelectrode 20 and undergoing a redox reaction. In this way, electrochemical cell 10 may be made even more selective.

As alluded to previously, electrochemical cell 10 may optionally be formed either partially or entirely on a single substrate chip by means of photolithography. Such a procedure would, of course, facilitate mass production of electrochemical cell 10 and may substantially reduce its manufacturing cost.

3. Electrochemical Cell Manufacture

Electrochemical cell 10 of the present invention may be manufactured in any of a number of different ways. The critical limitations regarding size and conductivity are set forth above. One presently preferred method of manufacturing electrochemical cell 10 is described below, wherein electrochemical cell 10 is formed with a glass tube 30.

The first step in forming electrochemical cell 10 is obtaining a suitable microelectrode 20. For example, microelectrode 20 may comprise a fiber of carbon material which is commercially available from a number of sources. A thin fiber of metal which is coated with a thick layer of silver (commonly referred to as "Wollaston wire") may also be used as microelectrode 20. Other fibers and thin wires of conductive material may also be employed.

As mentioned previously, the microelectrode may also be formed as a ring-type electrode 120, as illustrated in FIG. 3A. In fact, this is one of the easiest types of microelectrodes to manufacture. In order to manufacture a ring-type microelectrode 120, thin strands of quartz or glass 122 are drawn from a rod and thinly coated with a metal material 124 by means of conventional vapor deposition or screen printing techniques.

Once a suitable microelectrode 20 is obtained, it is next connected to a wire. For example, the microelectrode 20 is soldered to a wire 50 (see FIG. 1) by means of conventional tin solder. Alternatively, microelectrode 20 may be connected using conductive silver epoxy resin which is commercially available from a number of sources. There are, of course, numerous other ways in which microelectrode 20 may be connected to wire 50 which will be readily apparent to those skilled in the art.

Microelectrode 20 is next placed within some type of insulative holder. For example, microelectrode 20 is placed inside of a glass tube 30 having a predrawn capillary end 32. Such a glass holder is, for example, formed by drawing the end of a conventional Pyrex pipette so as to form a capillary tube.

If a Wollaston type wire is being used (that is, a wire which is comprised of a thin metal fiber surrounded by silver), it is next necessary to remove the silver so as to expose the inner conductive fiber. This may be done by immersing the capillary tip with the Wollaston wire therein in a solution of nitric acid, such that the silver coating is dissolved away from the lower half of the wire. The wire is then washed and allowed to dry. Alternatively, the silver coating can be electrochemically removed.

With microelectrode 20 thus in place within glass tube 30, the capillary tip of glass tube 30 is next sealed around microelectrode 20. There are a number of ways in which this may be accomplished.

First, capillary tip 30 may be sealed directly around microelectrode 20 by applying a vacuum to the opposite end of glass tube 30. Capillary tip 32 is thereafter gently heated, such as by means of a narrow bore oxy-acetylene torch Alternatively, microelectrode 20 may be sealed within capillary tip 32 by means of a sealant material. One type of sealant which is easily used is an epoxy material. As depicted in FIG. 1, epoxy material 34 is injected into glass tube 30 by blowing the small hole 36 near the end of glass tube 30 above capillary tip 32 prior to inserting microelectrode 20. Epoxy 34 is then injected through hole 36 (such as by means of a syringe) until the epoxy fills capillary tip 32.

After microelectrode 20 has been sealed within capillary tip 32, reference electrode 40 is provided on capillary tip 32. For example, a suitable conductive material may be vapor deposited on capillary tip 32. Alternatively, reference electrode 40 may be screen printed on capillary tip 32 or applied by means of an epoxy resin having fine metal particles suspended therein.

Next, an end portion of capillary tip 32 is cut off so as to expose the end disc 24 of microelectrode 20, as depicted in FIG. 2. The end of capillary tip 30 is then polished by using progressively finer grades of ground glass, such that the end of capillary tip 32 has a smooth surface.

If epoxy material 34 and glass tube 30 do not contain sufficient conductive material so as to function as an electrolyte for the size of electrochemical cell 10 constructed, the end of capillary tip 30 is then coated with an ionic substance of some type. Many suitable ionic substances were discussed previously and include most acids and bases and their associated salts.

Final preparations for using electrochemical cell 10 are then made by attaching a wire 54 to reference electrode 40. Again, wire 54 may be attached by means of a tin solder. Alternatively, wire 54 may be secured to reference electrode 40 by means of a commercially available silver epoxy. Electrochemical cell 10 is now ready for use.

4. System Operation

In using electrochemical cell 10, a potential difference is first applied between microelectrode 20 and reference electrode 40. The specific potential difference is selected such that it is at least as great as the redox potential for the substances which it is desired to detect.

After the necessary potential difference has been determined and applied, the few ions which are present either in the ambient surrounding or on the surface of electrochemical cell 10 adjacent disc 24 of microelectrode 20 migrate toward disc 24 so as to create a double layer having a high magnitude electric field. Significantly, only a few such ions are required since the cross-sectional diameter of microelectrode 20 is extremely small.

Thereafter, as atoms and molecules from the ambient environment enter the double layer adjacent microdisc 24, they undergo a redox reaction. A charge then passes across layers 32 and 34 to reference electrode 40, thereby causing a current to flow in the external circuit. This current can then be detected and measured.

Figure 4:
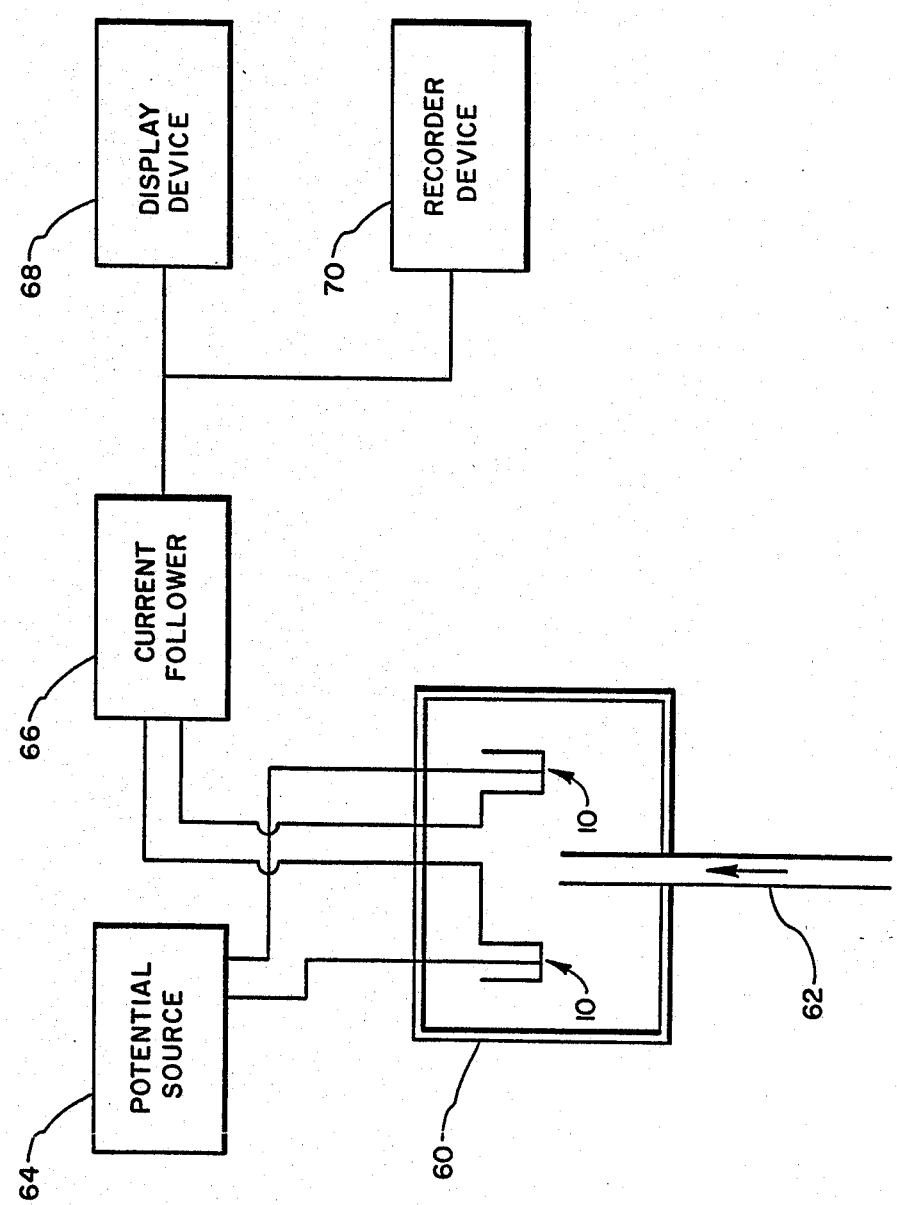
FIG. 4 is a general block diagram illustrating the circuitry which may be used in connection with the immobilized electrochemical cell of the present invention.

The external circuitry which is required in order to operate electrochemical cell 10 is well known by those skilled in the art and may have any of a number of suitable configurations. One example of the required circuitry is depicted in FIG. 4.

As shown, electrochemical cell 10 is placed within a shielding container 60 such as, for example, a Faraday cage. Cage 60 is also provided with a supply line 62 through which the substance passes which is to analyzed by electrochemical cell 10.

A potential source 64 is connected to the microelectrode 20 of electrochemical cell 10 so as to provide a stable source of potential to the microelectrode. The reference electrode 40 of electrochemical cell 10 is in turn connected to a current follower 66 which detects any current through the circuit and converts the current into a voltage reading. This voltage reading may then be supplied to a display device 68. Alternatively, or in combination, the output of current follower 66 may be provided to a suitable recorder device 70, such as, for example, a strip chart recorder.

The circuit components illustrated at 64, 66, 68, and 70 are readily available from a number of sources. For example, the potential source may comprise a waveform generator, Model 1800, manufactured by JAS Instrument Systems, Inc., Salt Lake City, Utah. Current follower 66 and display device 68 may be included in a single instrument such as Keithley Model 619 electrometer/multimeter, manufactured by Keithley Instruments, Inc., Cleveland, Ohio. Recorder device 70 may comprise an Omni Scriber recorder, manufactured by Houston Instruments, Austin, Tex.

In operation, potential source 64 is first adjusted so as to provide the potential at the microelectrode of the electrochemical cell which is required to detect the substance of interest. Sample material is then provided through input line 62 to box 60 so as to come in contact with the electrochemical cell.

Whenever an atom or molecule of the substance of interest comes into the double layer region adjacent the microelectrode of the electrochemical cell, a redox reaction occurs and a current is produced in the system and detected by current follower 66. Current follower 66 then converts the current reading into a voltage reading which can be monitored by display device 68 and/or recorder device 70.

The electrochemical cell may, therefore, be used to detect the presence of a substance having a given redox potential. Thus, the electrochemical cell may assist in identifying a particular substance by its redox potential. Also, the magnitude of the current produced through the system may also be monitored to give an indication of the concentration of the substance. Further, the data obtained over a period of time may be analyzed so as to better understand the redox reaction, such as, for example, the rate of electron transfer between molecules of the substance and the microelectrode of the electrochemical cell.

After a given period of operation, the electrodes of the electrochemical cell become coated with materials which have undergone the redox reaction. This may cause them to be somewhat less efficient and less sensitive. However, this situation can be easily remedied by providing an electrical pulse to electrochemical cell 10 which is opposite in polarization to its normal polarization. For example, if the microelectrode of electrochemical cell 10 is generally positively charged, a negative charge may be pulsed to the microelectrode of the electrochemical cell. This will cause the accumulated deposit on the electrodes to be burned off, thereby cleansing the electrodes of the electrochemical cell.

Optionally, as illustrated in FIG. 4, it may be desirable to use more than one electrochemical cell in a given environment. Each electrochemical cell may, for example, be provided with a different potential so as to detect different substances. Alternatively, a number of electrochemical cells may be arranged so as to detect the same substance, thereby increasing the total current through the system and consequently increasing the system's sensitivity. One possible way of providing an array of electrochemical cells is to photolithograph a plurality of electrochemical cells onto a single substrate chip.

It will be appreciated from the foregoing that the electrochemical cells of the present invention have a wide variety of different uses. Significantly, because the electrochemical cell is self-contained, it is capable of functioning in any gaseous or liquid environment. For example, electrochemical cell 10 may be placed within petroleum lines or chemical process lines. In such a position, the electrochemical cell can detect impurities in catalysts, leaks of reactants, or the presence of other undesirable substances. The electrochemical cell may also be used to determine the quality of a particular substance by monitoring its concentration and/or to discriminate between various types of substances used in various processing procedures.

The electrochemical cell of the present invention also promises to provide great benefits as a safety device. In the home or in industry, it may, for example be used to detect leaks of such substances as natural gas or carbon monoxide.

Similarly, the electrochemical cell may be used as a pollutant detector to detect the presence of heavy metals, carbon monoxide, or other undesirable substances. For example, the electrochemical cell could be used in public water supplies to monitor purity. The electrochemical cell could also be used tin the automotive industry or by health officials to monitor pollution in the atmosphere.

Electrochemical cells of the present invention also have a number of promising analytical applications. For example, such electrochemical cells may be used for a general purpose potential controlled liquid chromatography detector which can discriminate between species on the basis of their redox potentials. Similarly, electrochemical cells can be used in a general purpose, high sensitive gas chromatography detector for the same purpose.

5. Exemplary Illustrations

The following examples are exemplary of novel immobilized electrochemical cells which have been made and used in accordance with the present invention. Those of ordinary skill in the art will, of course, readily appreciate that an almost limitless number of materials and methods can be used to form the electrochemical cell and that the electrochemical cell can be used to detect virtually any substance which is capable of reduction/oxidation. The particular materials which are used to form the electrochemical cell, as well as the substances which the electrochemical cell is used to detect, will depend upon the particular application. Thus, the following examples are given by way of illustration.

EXAMPLE 1

An immobilized electrochemical cell within the scope of the present invention was made according to the following procedure.

A 2 ml volumetric pipette manufactured by American Dade Co., McGraw Park, Ill., and formed of soda glass was cut through the center of the bulb. The narrow ends of the pipette were then fused by heating with an oxy-acetylene torch. The fused ends were then heated and drawn out by pulling to a capillary tip such that the thickness of the glass (approximately 0.7 mm) was reduced and such that the outer diameter of the drawn ends was approximately 2 mm at the thinnest point.

The pipette was then cut at the thinnest point to provide two glass holders for microelectrodes. Thereafter, a small hole was blown approximately 1.5 cm from the capillary end of one of the holders to serve as an inlet for introduction of sealing material.

A platinum electrode wire approximately 15 mm long and 10 microns in diameter was used for the microelectrode. The microelectrode was soldered to a copper wire using tin solder and inserted into the holder such that it just protruded from the capillary end. "Super Strength Araldite" sealing resin manufactured by Ciba-Geigy (U.K.) Ltd., Plastic Division, Duxford, Cambridge, England, was then injected carefully into the holder through the above-mentioned hole using a plastic syringe until the resin first appeared around the protruding tip of the microelectrode. Then, a low noise coaxial cable was connected to the copper wire and was sealed into the large end of the glass holder opposite the capillary tip using heat-shrink sleeving (irradiated polyolefin).

After a curing period of at least 24 hours, the drawn end of the holder was coated with liquid bright platinum (No. 05-X, Engelhard Industries, East Newark, N.J.). The end was then heated to 650° C. in a tube furnace. The residual metal coating on the capillary end of the holder provided the reference electrode of the electrochemical cell.

A small end portion of the capillary end of the holder was then cut off using a glass file so as to expose the microelectrode. The cut capillary tip of the holder was thereafter ground flush using a rotating diamond disc. The residual metal coating on the capillary end of the holder provided the reference electrode of the electrochemical cell.

A small end portion of the capillary end of the holder was then cut off using a glass file so as to expose the microelectrode. The cut capillary tip of the holder was thereafter ground flush using a rotating diamond disc. the tip was then polished by hand on wet and dry emery paper, starting with grade B500 and working down in steps to grade P1200. Thereafter, the tip was polished with alumina (1 micron) water slurries and commercial metal polish (Brasso, household quality) on a polishing cloth.

The polished tip of the electrochemical cell was then dipped in a solution of sodium hydroxide (NaOH) to provide an immobilized ionic conductor between the microelectrode and the reference electrode. Finally, prior to use, a copper wire was secured to the reference electrode by means of a conductive silver epoxy (Epo-Tek H77) which is available from Epoxy Technology, Inc., Billerica, Mass.

EXAMPLE 2

An immobilized electrochemical cell within the scope of the present invention was made according to the procedures of Example 1, except that liquid bright palladium (No. 9752, Engelhard Industries) was used to form the reference electrode instead of liquid bright platinum.

EXAMPLE 3

An immobilized electrochemical cell within the scope of the present invention was made according to the procedures of Example 1, except that liquid bright gold (No. 4813, Engelhard Industries) was used to form the reference electrode instead of liquid bright platinum.

EXAMPLE 4

An immobilized electrochemical cell within the scope of the present invention was made according in the procedures of Example 1, except that a Wollaston wire manufactured by Goodfellow Metals Ltd., Cambridge, England, was used for the microelectrode instead of a platinum electrode wire.

After soldering the Wollaston wire to the copper wire support, the Wollaston wire electrode was passed through the capillary end of the glass holder such that approximately 10 mm of the Wollaston wire protruded. A gentle flow of air was then passed down through the tube to prevent corrosive vapors from dissolving the tin solder.

The silver coating was removed from approximately the bottom 5 mm of the Wollaston wire by immersing the capillary tip in a 50% nitric acid ($HNO_3$) solution for approximately four hours. The Wollaston wire was then washed with water and then rinsed with acetone and left to dry.

With the silver removed, a platinum electrode remained having a cross-sectional diameter of approximately 2.5 microns. This electrode was then sealed within the glass holder in accordance with the procedures of Example 1.

EXAMPLE 5

An immobilized electrochemical cell within the scope of the present invention was made according to the procedures of Example 4, except that liquid bright palladium (No. 9752, Engelhard Industries) was used to form the reference electrode instead of liquid bright platinum.

EXAMPLE 6

An immobilized electrochemical cell within the scope of the present invention was made according to the procedures of Example 4, except that liquid bright gold (No. 4813, Engelhard Industries) was used to form the reference electrode instead of liquid bright platinum.

EXAMPLE 7

An immobilized electrochemical cell within the scope of the present invention was made according to the procedures of Example 1, except that a carbon fiber was used for the microelectrode instead of the platinum electrode wire. The carbon fiber was 5 microns in diameter and 50 mm long and was obtained from Hercules Corp., Magna, Utah. Also, instead of using tin solder to connect the fiber to the copper wire, silver epoxy from Epoxy Technology, Inc., Billerica, Mass., was used.

EXAMPLE 8

An immobilized electrochemical cell within the scope of the present invention was made according to the procedures of Example 7, except that liquid bright palladium (No. 9752, Engelhard Industries) was used to form the reference electrode instead of liquid bright platinum.

EXAMPLE 9

An immobilized electrochemical cell within the scope of the present invention was made according to the procedures of Example 7, except that liquid bright gold (No. 4813, Engelhard Industries) was used to form the reference electrode instead of liquid bright platinum.

EXAMPLE 10

An immobilized electrochemical cell within the scope of the present invention was made according to the procedures of Example 1, except that, before injecting the sealing resin into the holder, the hole in the glass holder was temporarily sealed and the large end of the glass holder opposite the capillary tip was connected to a vacuum (water aspirator). The capillary end was then sealed around the microelectrode by very gently heating the capillary end beginning at the tip and working toward the larger portion of the holder using a narrow bore oxy-acetylene torch.

When the sealing procedure was complete, the sealing resin was injected into the holder according to the procedures of Example 1. However, since the capillary tip was already sealed, the resin did not appear around the tip of the microelectrode but remained inside the holder to provide support for the microelectrode.

EXAMPLE 11

An immobilized electrochemical cell within the scope of the present invention was made according to the procedures of Example 2, except that, before injecting the sealing resin into the holder, the hole in the glass holder was temporarily sealed and the large end of the glass holder opposite the capillary tip was connected to a vacuum (water aspirator). The capillary end was then sealed around the microelectrode by very gently heating the capillary end beginning at the tip and working toward the larger portion of the holder using a narrow bore oxy-acetylene torch.

When the sealing procedure was complete, the sealing resin was injected into the holder according to the procedures of Example 2. However, since the capillary tip was already sealed, the resin did not appear around the tip of the microelectrode but remained inside the holder to provide support for the microelectrode.

EXAMPLE 12

An immobilized electrochemical cell within the scope of the present invention was made according to the procedures of Example 3, except that, before injecting the sealing resin into the holder, the hole in the glass holder was temporarily sealed and the large end of the glass holder opposite the capillary tip was connected to a vacuum (water aspirator). The capillary end was then sealed around the microelectrode by very gently heating the capillary end beginning at the tip and working toward the larger portion of the holder using a narrow bore oxy-acetylene torch.

When the sealing procedure was complete, the sealing resin was injected into the holder according to the procedures of Example 3. However, since the capillary tip was already sealed, the resin did not appear around the tip of the microelectrode but remained inside the holder to provide support for the microelectrode.

EXAMPLE 13

An immobilized electrochemical cell within the scope of the present invention was made according to the procedures of Example 4, except that, before injecting the sealing resin into the holder, the hole in the glass holder was temporarily sealed and the large end of the glass holder opposite the capillary tip was connected to a vacuum (water aspirator). The capillary end was then sealed around the microelectrode by very gently heating the capillary end beginning at the tip and working toward the larger portion of the holder using a narrow bore oxy-acetylene torch.

When the sealing procedure was complete, the sealing resin was injected into the holder according to the procedures of Example 4. However, since the capillary tip was already sealed, the resin did not appear around the tip of the microelectrode but remained inside the holder to provide support for the microelectrode.

EXAMPLE 14

An immobilized electrochemical cell within the scope of the present invention was made according to the procedures of Example 5, except that, before injecting the sealing resin into the holder, the hole in the glass holder was temporarily sealed and the large end of the glass holder opposite the capillary tip was connected to a vacuum (water aspirator). The capillary end was then sealed around the microelectrode by very gently heating the capillary end beginning at the tip and working toward the larger portion of the holder using a narrow bore oxy-acetylene torch.

When the sealing procedure was complete, the sealing resin was injected into the holder according to the procedures of Example 5. However, since the capillary tip was already sealed, the resin did not appear around the tip of the microelectrode but remained inside the holder to provide support for the microelectrode.

EXAMPLE 15

An immobilized electrochemical cell within the scope of the present invention was made according to the procedures of Example 6, except that, before injecting the sealing resin into the holder, the hole in the glass holder was temporarily sealed and the large end of the glass holder opposite the capillary tip was connected to a vacuum (water aspirator). The capillary end was then sealed around the microelectrode by very gently heating the capillary end beginning at the tip and working toward the larger portion of the holder using a narrow bore oxy-acetylene torch.

When the sealing procedure was complete, the sealing resin was injected into the holder according to the procedures of Example 6. However, since the capillary tip was already sealed, the resin did not appear around the tip of the microelectrode but remained inside the holder to provide support for the microelectrode.

EXAMPLE 16

An immobilized electrochemical cell within the scope of the present invention was made according to the procedures of Example 1, except that the following procedure was used to form the microelectrode.

A thin quartz strand approximately 2 cm in length and 1-50 microns in diameter was drawn from a quartz rod (1 mm in diameter). The quartz strand was thereafter thinly coated (100 to 1000 angstrom thickness) with liquid bright gold (No. 4813, Engelhard Industries) and heated to 650° C. in a tube furnace. The gold coated quartz strands were then silver epoxied (using Epo-Tek 410 epoxy manufactured by Epoxy technology) to one end of a thin silver-plated copper wire and inserted into and sealed in the glass holder according to the procedures of Example 1. Using this technique, electrodes as small as 10 microns in diameter and 0.1 micron in thickness of the ring have been made.

EXAMPLE 17

An immobilized electrochemical cell within the scope of the present invention was made according to the procedures of Example 16, except that liquid bright palladium (No. 9752, Engelhard Industries) was used to form the reference electrode instead of liquid bright platinum.

EXAMPLE 18

An immobilized electrochemical cell within the scope of the present invention was made according to the procedures of Example 16, except that liquid bright gold (No. 4813, Engelhard Industries) was used to form the reference electrode instead of liquid bright platinum.

EXAMPLE 19

An immobilized electrochemical cell within the scope of the present invention was made according to the procedures of Example 16, except that the quartz strand was coated with liquid bright palladium (No. 9752, Engelhard Industries) to form the microelectrode instead of liquid bright gold.

EXAMPLE 20

An immobilized electrochemical cell within the scope of the present invention was made according to the procedures of Example 19, except that liquid bright palladium (No. 9752, Engelhard Industries) was used to form the reference electrode instead of liquid bright platinum.

EXAMPLE 21

An immobilized electrochemical cell within the scope of the present invention was made according to the procedures of Example 19, except that liquid bright gold (No. 4813, Engelhard Industries) was used to form the reference electrode instead of liquid bright platinum.

EXAMPLE 22

An immobilized electrochemical cell within the scope of the present invention was made according to the procedures of Example 16, except that the quartz strand was coated with liquid bright platinum (No. 05-X, Engelhard Industries) to form the microelectrode instead of liquid bright gold.

EXAMPLE 23

An immobilized electrochemical cell within the scope of the present invention was made according to the procedures of Example 22, except that liquid bright palladium (No. 9752, Engelhard Industries) was used to form the reference electrode instead of liquid bright platinum.

EXAMPLE 24

An immobilized electrochemical cell within the scope of the present invention was made according to the procedures of Example 22, except that liquid bright gold (No. 4813, Engelhard Industries) was used to form the reference electrode instead of liquid bright platinum.

EXAMPLE 25

In Example 25, a system configuration substantially similar to the configuration illustrated in FIG. 4 was used, except that only a single electrochemical cell 10 was used. The input line 62 was connected to the output of a model 700 Hewlett-Packard gas chromatograph, and recorder device 70 comprised a two pen strip chart recorder manufactured by Houston Instruments, under the name "Omni Scriber."

The following experimental conditions were employed:
Carrier gas: Nitrogen ($N_2$)
Carrier gas flow rate: 30 $cm^3$/min
Packed column used in the gas chromatograph: 6 feet of carbowax 20M
Gas chromatograph oven temperature: 80° C.
Detector Temperature (Thermal Conductivity Detector, "TCD"): 150° C.
Injection port temperature: 150° C.

An immobilized electrochemical cell within the scope of the present invention was made utilizing the components and procedures of Example 8. The electrochemical cell was then placed within a faraday cage, and a potential of approximately 3 volts was applied between the microelectrode and the reference electrode, the microelectrode being the anode. The output of the gas chromatograph was blown over the surface of the electrochemical cell.

Different amounts of water were injected to the gas chromatograph, namely 1.0, 0.75, and 0.5 microliters, and the responses were recorded. The area under each of the microelectrode curves on recorder 70 were then compared.

It was observed that the area under the microelectrode curve was greatest for the 1 microliter injection and that the area was smallest for the 0.5 microliter injection. Furthermore, the areas under the curves were in all cases proportional to the amount of water injected, to within experimental error. This confirms that the response of the electrochemical cell is dependent upon concentration and can, therefore, be used to determine the concentration of a substance in a given environment.

EXAMPLE 26

In Example 26, the methods and procedures of Example 25 were repeated, except that the carbon microelectrode was the cathode. It was observed that the response of the electrochemical cell, as reflected on recorded 70, was inverted in comparison with the responses obtained in Example 25. This is the expected result, since current should now flow through the circuit in the opposite direction.

EXAMPLES 27-51

In Examples 27-51, the methods and procedures of Example 25 were used, except that two microliters of different compounds were injected into the gas chromatograph in place of the three samples of water, and the output of the gas chromatograph was then blown over the electrochemical cell. Twenty-five of the compounds tested are reported in Table I below as examples. Table I indicates whether the electrochemical cell responded to the compound or not. The lack of a response in some cases is due to the fact that the potential between the electrodes was only 3 volts and, possibly, to the particular reactive properties of the materials used to form the electrochemical cell. Thus, Table I illustrates that an electrochemical cell within the scope of the present invention can be used to discriminate between different compounds.

TABLE I

| Example No. | Compounds | Microelectrode Responded Yes | No |
|---|---|---|---|
| 27 | Water | X | |
| 28 | Ethanol | X | |
| 29 | Ammonia (0.1 N) | X | |
| 30 | Isopropylamine | X | |
| 31 | Hexane | | X |
| 32 | Acetone | very weak | |
| 33 | Aniline | very weak | |
| 34 | Acetic Acid | | X |
| 35 | N—Methyl Acetamide | | X |
| 36 | Formic Acid | X | |
| 37 | Triethylamine | X | |
| 38 | N—Methylamine | X | |
| 39 | Nitrobenze | very weak | |
| 40 | 3 Bromothiophene | very weak | |
| 41 | N,N dimethyl acetamide | very weak | |
| 42 | Ethyl acetate | | X |
| 43 | Ethylene dichloride | X | |
| 44 | Benzonitrile | X | |
| 45 | Acetonitrile | X | |
| 46 | Ethyl benzene | X | |
| 47 | Trichloro, trifloroethane | | X |
| 48 | Toluene | X | |
| 49 | Cyclohexanone | X | |
| 50 | Carbon Monoxide (1% in Nitrogen) | X | |
| 51 | Vinyl Chloride (10 ppm in air) | X | |

EXAMPLE 52

In Example 52, the methods and procedures of Example 25 were used, except that two microliters of N-methylamine wee injected into the gas chromatograph in place of the three samples of water, and the potential between the microelectrode and the reference electrode was varied between 1 volt and 3 volts. The output of the gas chromatograph was then blown over the electrochemical cell.

It was observed that the response of the electrochemical cell was greatest at a potential difference of 2.5 volts and least at a potential difference of 1 volt. This illustrates that each compound has an optimum potential at which it will undergo a redox reaction and that this optimum potential can thus be used to select which compounds will be detected by the electrochemical cell.

EXAMPLES 53-65

In Examples 53-56, the methods and procedures of Example 25 were used, except that two microliters of different compounds were injected into the gas chromatograph in place of the three samples of water, and the output of the gas chromatograph was then blown over the electrochemical cell. The response of the microelectrode (mV) was then compared with the response of the TCD of the gas chromatograph (mV). Thirteen of the compounds tested are reported in Table II below as examples. Table II indicates the ratio of the response of the microelectrode to the response of the TCD for each compound.

TABLE II

| Example No. | Compounds | Microelectrode Response / TCD Response |
|---|---|---|
| 53 | Ethyl Acetate | 0 |
| 54 | Ethylene Dichloride | 24 |
| 55 | Benzo nitrile | 172 |
| 56 | Ethyl Benzene | 6 |
| 57 | Acetonitrile | 16 |
| 58 | 1,1,2 Trichloro, trifloroethane | 0 |
| 59 | Toluene | 4 |
| 60 | Cyclohexanone | 10 |
| 61 | N—Methylamine (40% in water) | 12.5 |
| 62 | Triethylamine | 100 |
| 63 | N—Methylacetamide | 0 |
| 64 | Formic Acid | 1.33 |
| 65 | Ammonia (0.1 N) | 13 |

EXAMPLES 66-79

In Examples 66-79, the methods and procedures of Example 25 were used, except that the electrochemical cell was made according to the procedures of Example 16 and two microliters of different compounds were injected into the gas chromatograph in place of the three samples of water. In addition, SE 30 gas chromatograph column was used in place of carbowax 20M, and the output of the gas chromatograph was blow over the electrochemical call.

The response of the microelectrode (mV) was then compared with the response of the TCD of the gas chromatograph (mV). Fourteen of the compounds tested are reported in Table III below as examples. Table III indicates the ratio of the response of the microelectrode to the response of the TCD for each compound.

TABLE III

| Example No. | Compounds | Microelectrode Response / TCD Response |
|---|---|---|
| 66 | Ethanol | 1.9 |
| 67 | Ethylene dichloride | 0.08 |
| 68 | Propylamine and Triethylamine | 0.05 |
| 69 | N—Methylamine (40% in $H_2O$) | 6.3 |
| 70 | Aniline | 100 |
| 71 | Acetonitrile | 0.75 |
| 72 | Toluene | 0.22 |
| 73 | Ethyl Benzene | 0.15 |
| 74 | Benzonitrile | 30 |
| 75 | Acetone | 0.12 |

TABLE III-continued

| Example No. | Compounds | Microelectrode Response TCD Response |
|---|---|---|
| 76 | Hexane | 0 |
| 77 | Carbon tetrachloride | 0 |
| 78 | Cyclohexanone | 3.8 |
| 79 | Tert-butyl benzene | 0 |

EXAMPLES 80-85

In Examples 80-85, the methods and procedures of Example 25 were used, except that two microliters of different compounds were injected into the gas chromatograph in place of the three samples of water, and the output of the gas chromatograph was then blown over the electrochemical cell. In addition, the electrochemical cell was made according to the procedures of Example 7 and SE 30 column was used for the gas chromatograph instead of carbowax 20M.

Six of the compounds tested are reported in Table IV below as examples. Table IV indicates whether the electrochemical cell responded to the compound or not. The lack of a response in some cases is due to the fact that the potential between the electrodes was only 3 volts and, possibly, to the particular reactive properties of the materials used to form the electrochemical cell. Thus, Table IV illustrates that an electrochemical cell within the scope of the present invention can be used to discriminate between different compounds.

TABLE IV

| Example No. | Compounds Tested | Microelectrode Responded Yes | No |
|---|---|---|---|
| 80 | N—Methylamine | X | |
| 81 | Ethanol | X | |
| 82 | Acetone | | X |
| 83 | Formic Acid | X | |
| 84 | Hexane | | X |
| 85 | Diethylether | | X |

6. Summary

From the above discussion, it will be appreciated that the present invention provides an immobilized electrochemical cell which can be used in virtually any gaseous or liquid environment, since it requires no solvent and no purposefully added electrolyte. Moreover, the electrochemical cell of the present invention is a simple system comprising merely two electrodes, but it is able to provide highly accurate results.

Since the current through the electrochemical cell of the present invention is small, the potential error is likewise very small, even in the presence of highly resistive media. Moreover, unlike prior art devices, the potential error can actually be calculated for any particular system configuration.

The small size of the electrochemical cell of the present invention also leads to extremely small capacitive currents. Moreover, the electrochemical cell of the present invention approaches near perfect spherical diffusion, and it is not generally limited by diffusion except in the case of extremely fast reactions. Significantly, these advantages are accomplished through simple mechanisms and low cost.

The invention may be embodied in other specific forms without departing from its spirt or essential characteristics. The described embodiments are to be considered in all respects only as illustrative and not restrictive. the scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An immobilized electrochemical cell characterized in that the cell requires no self-contained electrolytic substance for ionization, the cell comprising:
   a microelectrode having a cross-section diameter of less than about twenty-five (25) microns;
   a reference electrode positioned less than about three (3) millimeters from the microelectrode; and
   an insulative material positioned between the microelectrode and the reference electrode so as to maintain the electrodes a substantially fixed distance apart, the insulative material being dielectric but capable of ambient ion flow at the surface thereof for forming a charged layer of ions adjacent the microelectrode when a potential difference is applied between the microelectrode and the reference electrode, wherein a high magnitude electric field is created adjacent the microelectrode in the presence of minimal ambient ions, enabling electrochemical analysis in gaseous, liquid and solid environments.

2. An immobilized electrochemical cell characterized in that the cell requires no self-contained electrolytic substance for ionization, the cell comprising:
   an insulative holder comprising a tube having an outer cross-sectional diameter of less than about six (6) millimeters, said tube having a tip;
   a microelectrode sealed within the tube of the holder so as to extend to the tip, said microelectrode having a cross-sectional diameter of less than about twenty-five (25) microns; and
   a reference electrode coating at least a portion of the tube of the holder so as to surround the microelectrode;
   the tip of the tube of the insulative holder being formed of insulative material which is dielectric but capable of ambient ion flow at the surface thereof forming a charged layer of ions adjacent the microelectrode when a potential difference is applied between the microelectrode and the reference electrode, whereby a high magnitude electric field is created adjacent the microelectrode in the presence of minimal ambient ions, enabling electrochemical analysis in gaseous, liquid and solid environments.

3. An electrochemical sensor system, comprising:
   an electrochemical cell characterized in that the cell requires no self-contained electrolytic substance for ionization, the cell comprising:
   a microelectrode having a cross-sectional diameter of less than about twenty-five (25) microns;
   a reference electrode positioned less than about three (3) millimeters from the microelectrode; and
   an insulative material positioned between the microelectrode and the reference electrode so as to maintain the electrodes a substantially fixed distance apart, the insulative material being dielectric but capable of ambient ion flow at the surface thereof for forming a charged layer of ions adjacent the microelectrode when a potential difference is applied between the microelectrode and the reference electrode, whereby a high magnitude electric field is created adjacent the microelectrode in the presence of minimal ambient ions, enabling electrochemical analysis in gaseous, liquid and solid environments;

a potential source electrically connected to the microelectrode; and means electrically connected to the reference electrode for detecting an electrical current between the microelectrode and the reference electrode.

4. A method for manufacturing an immobilized electrochemical cell which requires no self-contained electrolytic substance for ionization, the method comprising the steps of:

inserting a microelectrode having a cross-sectional diameter of less than about twenty-five (25) microns into an insulative holder which comprises a tube having an outer cross-sectional diameter of less than about six (6) millimeters and which is formed of an insulative material which is dielectric but capable of ambient ion flow at the surface thereof;

sealing the microelectrode within the tube of the insulative holder; and coating the tube of the insulative holder with a conductive material so as to form a reference electrode surrounding the microelectrode, the cell being operable for forming a charged layer of ions adjacent the microelectrode which a potential difference is applied between the microelectrode and the reference electrode, whereby a high magnitude electric field is created adjacent the microelectrode in the presence of minimal ambient ions, enabling electrochemical analysis in gaseous, liquid and sold environments

* * * * *

UNITED STATES PATENT AND TRADEMARK OFFICE
CERTIFICATE OF CORRECTION

PATENT NO. : 4,783,250

DATED : November 8, 1988

INVENTOR(S) : B. Stanley Pons et al

It is certified that error appears in the above-identified patent and that said Letters Patent is hereby corrected as shown below:

Column 1, Lines 38-39, reads "electrochemicaloxidation" but should read -- electrochemical oxidation --.

Column 2, Line 23, reads "mist" but should read -- most --.

Column 4, Line 52, reads "relay" but should read -- rely --.

Column 6, Line 7, reads "call" but should read -- cell --.

Column 6, Line 8, reads "call" but should read -- cell --.

Column 8, Line 41, reads "1" (boldface type) but should read -- 1 -- (non-boldface type).

Column 8, Line 57, reads "1" (boldface type) but should read -- 1 -- (non-boldface type).

Column 14, Line 22, after "torch" add -- . --.

Column 16, Line 15, reads "cleansing" but should read -- cleaning --.

Column 16, Line 52, reads "tin" but should read -- in --.

Column 17, Lines 54-60, delete all of lines 54-60.

Column 21, Line 22, reads "Epoxy technology" but should read -- Epoxy Technology --.

Column 23, Line 39, reads "N--Methyl Acetamide" but should read -- N-Methyl Acetamide --.

UNITED STATES PATENT AND TRADEMARK OFFICE
CERTIFICATE OF CORRECTION

PATENT NO. : 4,783,250

DATED : November 8, 1988

INVENTOR(S) : B. Stanley Pons et al

It is certified that error appears in the above-identified patent and that said Letters Patent is hereby corrected as shown below:

Column 23, Line 42, reads "N--Methylamine" but should read -- N-Methylamine --.

Column 23, Line 60, reads "wee" but should read -- were --.

Column 24, Lines 22-23, reads "Microelectrode Response TCD Response " but should read -- Microelectrode Response TCD Response --.

Column 24, Line 31, reads "N--Methylamine" but should read -- N-Methylamine --.

Column 24, Line 33, reads "N--Methylacetamide" but should read -- N-Methylacetamide --.

Column 24, Line 47, reads "blow" but should read -- blown --.

Column 24, Line 48, reads "call" but should read -- cell --.

Column 24, Lines 57-58 reads "Microelectrode Response TCD Response " but should read -- Microelectrode Response TCD Response --.

Column 24, Line 63, reads "N--Methylamine" but should read -- N-Methylamine --.

Column 25, Lines 2-3, reads "Microelectrode Response TCD Response " but should read -- Microelectrode Response TCD Response --.

UNITED STATES PATENT AND TRADEMARK OFFICE
CERTIFICATE OF CORRECTION

PATENT NO. : 4,783,250

DATED : November 8, 1988

INVENTOR(S) : B. Stanley Pons et al

Page 3 of 3

It is certified that error appears in the above-identified patent and that said Letters Patent is hereby corrected as shown below:

Column 25, Line 34, reads "N--Methylamine" but should read -- N-Methylamine --.

Column 25, Line 67, reads "the" (first occurrence) but should read -- The --.

Column 26, Line 9, reads "cross-section diameter" but should read -- cross-sectional diameter --.

Column 26, Line 21, reads "wherein" but should read -- whereby --.

Column 26, Line 43, after "thereof" add -- for --.

Column 28, Line 10, reads "which" but should read -- when --.

Signed and Sealed this

Twenty-second Day of September, 1992

Attest:

DOUGLAS B. COMER

Attesting Officer

Acting Commissioner of Patents and Trademarks